(12) United States Patent
Cabibihan et al.

(10) Patent No.: US 12,109,000 B2
(45) Date of Patent: Oct. 8, 2024

(54) TACTILE SENSOR, A SURGICAL INSTRUMENT HAVING THE SAME, AND A METHOD OF MANUFACTURING THE SAME

(71) Applicants: QATAR FOUNDATION, Doha (QA); QATAR UNIVERSITY, Doha (QA)

(72) Inventors: John-John Cabibihan, Doha (QA); Kishor Kumar Sadasivuni, Doha (QA); Anas Tahir, Doha (QA); Julien Abinahed, Doha (QA); Nikhil Navkar, Doha (QA); Abdulla Al-Ansari, Doha (QA)

(73) Assignees: QATAR FOUNDATION FOR EDUCATION, SCIENCE AND COMMUNITY DEVELOPMENT;, Doha (QA); QATAR UNIVERSITY, Doha (QA)

( * ) Notice: Subject to any disclaimer, the term of this patent is extended or adjusted under 35 U.S.C. 154(b) by 445 days.

(21) Appl. No.: 17/609,551

(22) PCT Filed: May 9, 2019

(86) PCT No.: PCT/QA2019/050011
§ 371 (c)(1),
(2) Date: Nov. 8, 2021

(87) PCT Pub. No.: WO2020/226524
PCT Pub. Date: Nov. 12, 2020

(65) Prior Publication Data
US 2022/0202519 A1    Jun. 30, 2022

(51) Int. Cl.
*A61B 34/00* (2016.01)
*A61B 17/28* (2006.01)
(Continued)

(52) U.S. Cl.
CPC .............. *A61B 34/76* (2016.02); *A61B 17/28* (2013.01); *A61B 34/37* (2016.02); *G01L 1/16* (2013.01); *A61B 2017/0011* (2013.01)

(58) Field of Classification Search
CPC ......... A61B 34/76; A61B 17/28; A61B 34/37; A61B 2017/0011; A61B 2090/065; A61B 34/30; G01L 1/16; H10N 30/85
(Continued)

(56) References Cited

U.S. PATENT DOCUMENTS

| 2011/0046637 A1* | 2/2011 | Patel .................. A61B 17/29 606/130 |
| 2012/0055257 A1 | 3/2012 | Shaw-Klein |
| 2013/0274712 A1 | 10/2013 | Schecter |

FOREIGN PATENT DOCUMENTS

KR    20170084861 A  *  7/2017

OTHER PUBLICATIONS

Souri et al Article, pp. 579-586, 2015.*
(Continued)

*Primary Examiner* — Robert R Raevis
(74) *Attorney, Agent, or Firm* — K&L Gates

(57) ABSTRACT

A tactile sensor, a surgical instrument, and a method of making the tactile sensor are provided. In one embodiment, a tactile sensor includes a first electrode, a second electrode, and an intermediate layer between the first electrode and the second electrode. The intermediate layer includes a polyurethane-zinc oxide nanocomposite. Further, one or both of the first and second electrodes may include a silver conductive paste.

7 Claims, 4 Drawing Sheets
(2 of 4 Drawing Sheet(s) Filed in Color)

(51) Int. Cl.
A61B 34/37 (2016.01)
G01L 1/16 (2006.01)
A61B 17/00 (2006.01)

(58) Field of Classification Search
USPC .......... 73/1.15, 1.48, 35.11, 35.13, 775, 776, 73/862.042, 862.473, 862, 541, 862.625, 73/862.68, 514.34, 753; 210/320–271
See application file for complete search history.

(56) References Cited

OTHER PUBLICATIONS

International Search Report for related International Application No. PCT/QA2019/050011; report dated Nov. 12, 2020; (2 pages).
Written Opinion for related International Application No. PCT/QA2019/050011; report dated Nov. 12, 2020; (5 pages).
Souri et al. "A zinc oxide/polyurethane-based generator composite as a self-powered sensor for traffic flow monitoring" Composite Structures vol. 134, Dec. 15, 2015, pp. 579-586; entire document; especially Fig. 1, Fig.3, p. 580; Retrieved on Jul. 24, 2020 from website:https://www.sciencedirect.com/science/article/pii/S0263822315008089.
Zhu et al. "Functional Electrical Stimulation by Nanogenerator with 58 V Output Voltage" Nano Lett. 2012, 12, 6, 3086-3090; May 17, 2012; entire document; esecially p. A; Retrieved on Jul. 24, 2020 from website:https://pubs.acs.org/doi/abs/10.1021/nl300972f.
Lee et al. "Highly Sensitive and Multifunctional Tactile Sensor Using Free-standing ZnO/PVDF Thin Film with Graphene Electrodes for Pressure and Temperature Monitoring" Scientific Reports vol. 5, Article No. 7887 (2015) Jan. 20, 2015; entire document; especially Fig. 4, p. 2; Retrieved on Jul. 13, 2020 from website: https://www.nature.com/articles/srep07887.
Qasaimeh, et al.; "An Endoscopic Grasper With Corrugated Plate-Shaped Tactile Sensors"; Journal of Mechanics of Materials and Structures; May 2009; (16 pages).
Meyers; "Piezoelectric nanocomposite sensors assembled using zinc oxide nanoparticles and poly(vinylidene fluoride)"; ResearchGate; Jul. 2013; (18 pages).
Navkar, et al; "Experimental characterization of a tactile sensor for surgical applications"; 2018; IEEE Conference Publication; (3 pages).

* cited by examiner

| Average Forces | Average Voltages |
|---|---|
| 0.45 | 0.21 |
| 1.14 | 0.47 |
| 1.63 | 0.68 |
| 2.01 | 0.87 |
| 2.42 | 1.07 |
| 3.12 | 1.35 |
| 4.19 | 1.57 |
| 5.41 | 1.90 |
| 6.15 | 2.06 |
| 7.14 | 2.34 |

TACTILE SENSOR, A SURGICAL INSTRUMENT HAVING THE SAME, AND A METHOD OF MANUFACTURING THE SAME

CROSS-REFERENCE TO RELATED APPLICATIONS

The present application is a National Stage filing under 35 U.S.C. 371 of International Application No. PCT/QA2020/050006, filed on May 10, 2020, the entire contents of which are being incorporated herein by reference.

BACKGROUND

Over the past decades, robots have gained significant attention and have been playing an important role in daily living, for healthcare applications and for other industrial applications. For example, robots are becoming increasingly popular for Minimal Invasive Surgery (MIS). Robots provide clinicians with additional capabilities, for example, in remote surgery, in scaling the surgeon's movement, tremor reduction, and potentially the promise of increased automation. As surgeries move towards a minimally invasive approach to reduce scarring and increase a patient's recovery time, robotic minimally invasive surgeries offer additional benefits to the patients and surgeons alike. However, the lack of haptic force feedback for surgeons limits them from accurate tissue palpation and the identification of contact interactions of the surgical instruments with their patient's tissues and organs.

SUMMARY

The present disclosure generally relates to a tactile sensor, a surgical instrument including a tactile sensor and a method of manufacturing a tactile sensor.

In light of the present disclosure, and without limiting the scope of the disclosure in any way, in an aspect of the present disclosure, which may be combined with any other aspect listed herein unless specified otherwise, a tactile sensor is provided. The tactile sensor includes a first electrode, a second electrode, and an intermediate layer between the first electrode and the second electrode. The intermediate layer includes a polyurethane-zinc oxide nanocomposite.

In an aspect of the present disclosure, which may be combined with any other aspect listed herein unless specified otherwise, the first electrode includes a silver conductive paste.

In an aspect of the present disclosure, which may be combined with any other aspect listed herein unless specified otherwise, the second electrode includes a silver conductive paste.

In an aspect of the present disclosure, which may be combined with any other aspect listed herein unless specified otherwise, a tactile sensor includes a first conductive wire and a second conductive wire.

In an aspect of the present disclosure, which may be combined with any other aspect listed herein unless specified otherwise, the first conductive wire is provided on the first electrode.

In an aspect of the present disclosure, which may be combined with any other aspect listed herein unless specified otherwise, the second conductive wire is provided on the second electrode.

In an aspect of the present disclosure, which may be combined with any other aspect listed herein unless specified otherwise, the first conductive wire and the second conductive wire include copper.

In an aspect of the present disclosure, which may be combined with any other aspect listed herein unless specified otherwise, the first conductive wire and the second conductive wire include silver.

In an aspect of the present disclosure, which may be combined with any other aspect listed herein unless specified otherwise, a tactile sensor includes a top layer and a bottom layer.

In an aspect of the present disclosure, which may be combined with any other aspect listed herein unless specified otherwise, the top layer is provided on the first conductive wire.

In an aspect of the present disclosure, which may be combined with any other aspect listed herein unless specified otherwise, the bottom layer is provided on the second conductive wire.

In an aspect of the present disclosure, which may be combined with any other aspect listed herein unless specified otherwise, the top layer and the bottom layer include aluminum.

In an aspect of the present disclosure, which may be combined with any other aspect listed herein unless specified otherwise, a surgical instrument is provided. The surgical instrument includes a grasper, and a tactile sensor provided on the grasper. The tactile sensor further includes a first electrode, a second electrode, and an intermediate layer between the first electrode and the second electrode. The intermediate layer includes a polyurethane-zinc oxide nanocomposite.

In an aspect of the present disclosure, which may be combined with any other aspect listed herein unless specified otherwise, the first electrode includes a silver conductive paste.

In an aspect of the present disclosure, which may be combined with any other aspect listed herein unless specified otherwise, the second electrode includes a silver conductive paste.

In an aspect of the present disclosure, which may be combined with any other aspect listed herein unless specified otherwise, a tactile sensor further comprises a first conductive wire and a second conductive wire.

In an aspect of the present disclosure, which may be combined with any other aspect listed herein unless specified otherwise, the first conductive wire and the second conductive wire include copper.

In an aspect of the present disclosure, which may be combined with any other aspect listed herein unless specified otherwise, the first conductive wire and the second conductive wire include silver.

In an aspect of the present disclosure, which may be combined with any other aspect listed herein unless specified otherwise, a tactile sensor further comprises a top layer and a bottom layer.

In an aspect of the present disclosure, which may be combined with any other aspect listed herein unless specified otherwise, a method of producing a tactile sensor is provided. The method includes providing a first mixture including polyurethane and a first solvent, providing a second mixture including zinc oxide and a second solvent, mixing the first mixture with the second mixture to form a third mixture, removing solvent from the third mixture, adding polyurethane into the third mixture to form a film, and providing electrodes on the film.

Additional features and advantages of the device, surgical instrument, and method are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein. Moreover, it should be noted that the language used in the specification has been principally selected for readability and instructional purposes, and not to limit the scope of the inventive subject matter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Features and advantages of the present disclosure including a tactile sensor, a surgical instrument and a method described herein may be better understood by reference to the accompanying drawings in which.

The reader will appreciate the foregoing details, as well as others, upon considering the following detailed description of certain non-limiting embodiments of the present disclosure. The reader may also comprehend certain of such additional details upon using the present technology including devices, instruments and methods described herein.

DETAILED DESCRIPTION

Tactile haptic feedback can help the surgeons to register the forces applied over a grasper of a surgical tooltip and can reduce the learning time for novice surgeons and help prevent injuries on the patient. Forces applied to a specific tissue during surgery are dependent on the texture of the tissue. 3D imaging-based techniques over the high-quality images obtained from the camera are the most popular methods to identify the forces and provide feedback to surgeons. However, the image-based force analysis does not provide realistic tactile feedback to the surgeons' hands, and it takes a longer time and practice for a novice surgeon to get comfortable during surgery.

Nowadays, robot-based minimally invasive surgery is getting popular, but the force registration over the graspers of surgical tooltips faces the same problem of vision-based analysis.

One of the goals of the present disclosure is to make the force registration of the graspers over the tissue during surgery as accurate and reliable as possible. With sensor-based technology, a tactile feedback can be provided to the console over the hands of surgeons, and the surgeons can have an accurate and reliable feeling from the forces applied on the graspers of the surgical instruments.

The present disclosure, in part, is directed to a tactile sensor device, a surgical instrument having a tactile sensor device and a method to make a tactile sensor device. The benefits of the tactile sensor device, the surgical instrument, and the method for making the tactile sensor according to the present disclosure are, for example, non-invasive, user friendly, fast and robust, low cost, excellent performance, biocompatible, and eco-friendly. The present disclosure provides technologies configured to help make the force registration of the graspers over the tissue during surgery as accurate and reliable as possible with minimum time delays.

Figure 1:
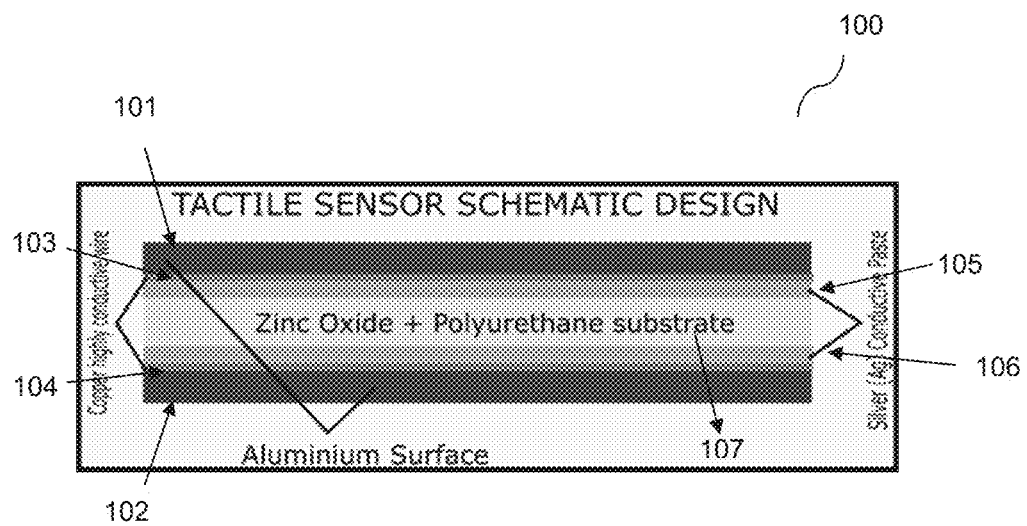
FIG. 1 is a schematic illustration of a tactile sensor according to an embodiment of the present disclosure.

Referring to FIG. 1, the illustrated embodiment of the tactile sensor device includes a top layer 101 and a bottom layer 102, a top conductive wire 103, a bottom conductive wire 104, an upper electrode 105, a lower electrode 106, and an intermediate layer 107 provided between the upper electrode 105 and the lower electrode 106.

The intermediate layer 107 may include a nanocomposite. The nanocomposite generally comprises polymer matrices and nanoscale conductive fillers embedded in matrices. The nanoscale conductive fillers may include one or both of metal-based fillers and carbon-based fillers. As a non-limiting example, the intermediate layer 107 may include a polyurethane-zinc oxide nanocomposite according to an embodiment of the present disclosure.

The upper electrode 105 and the lower electrode 106 are provided on the intermediate layer 107. The upper electrode 105 and the lower electrode 106 may include a silver (Ag) conductive paste, a gold (Au) conductive paste, an aluminum conductive paste, a copper conductive paste or other conductive paste or any combination thereof. The upper electrode 105 may include a same conductive paste as the lower electrode 106. The upper electrode 105 may include a different conductive paste from the lower electrode 106 according to an embodiment of the present disclosure.

The top conductive wire 103 is provided on the upper electrode 105 and the bottom conductive wire 104 is provided on the lower electrode 106 according to an embodiment. The top conductive wire 103 and the bottom conductive wire 104 may include copper, silver (Ag), gold (Au), aluminum or the like or any combination thereof. The top conductive wire 103 may include a same conductive material as the bottom conductive wire 104. The top conductive wire 103 may include a different conductive material from the bottom conductive wire 104 according to an embodiment of the present disclosure.

As illustrated in FIG. 1, the top layer 101 is provided on the top conductive wire 103, and the bottom layer 102 is provided on the bottom conductive wire 104. The top layer 101 and the bottom layer 102 may include aluminum, silver (Ag), gold (Au) or the like or any combination thereof. The top layer 101 may include a same material as the bottom layer 102. The top layer 101 may include a different material from the bottom layer 102 according to another embodiment of the present disclosure.

Figure 2:
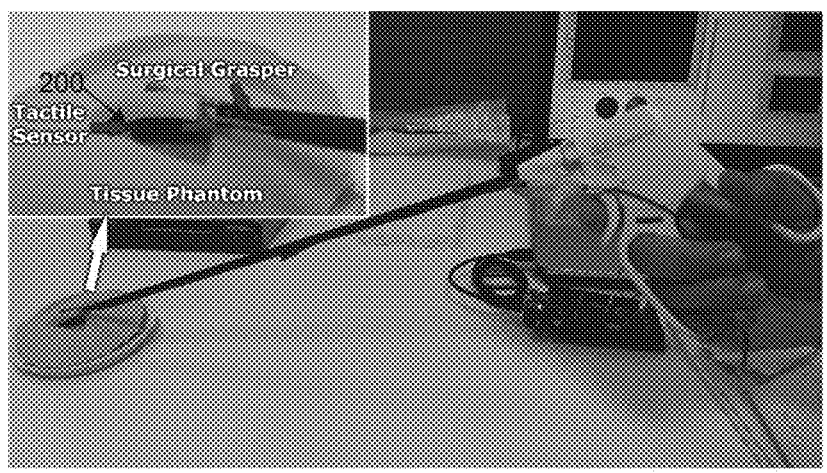
FIG. 2 is an illustration of a tactile sensor provided on a surgical tool according to an embodiment of the present disclosure.

Referring to FIG. 2, an embodiment of a tactile sensor 200 provided on a surgical tool is illustrated. The tactile sensor 200 is configured to obtain the force profile across the sensor. For example, the tactile sensor is configured to measure the electric discharge due to piezoelectricity of the tactile sensor and detect different forces applied thereon. The tactile sensor 200 is provided on a grasper of the hand-held surgical tool. The force reading was obtained from the tactile sensor by the voltage signal reading from the tactile sensor. Different forces were applied manually and the robustness was also calculated. The tactile sensor 200 may be embedded into the grasper of robotic or laparoscopic surgical tooltip or the like according to an embodiment of the present disclosure.

Figure 3:
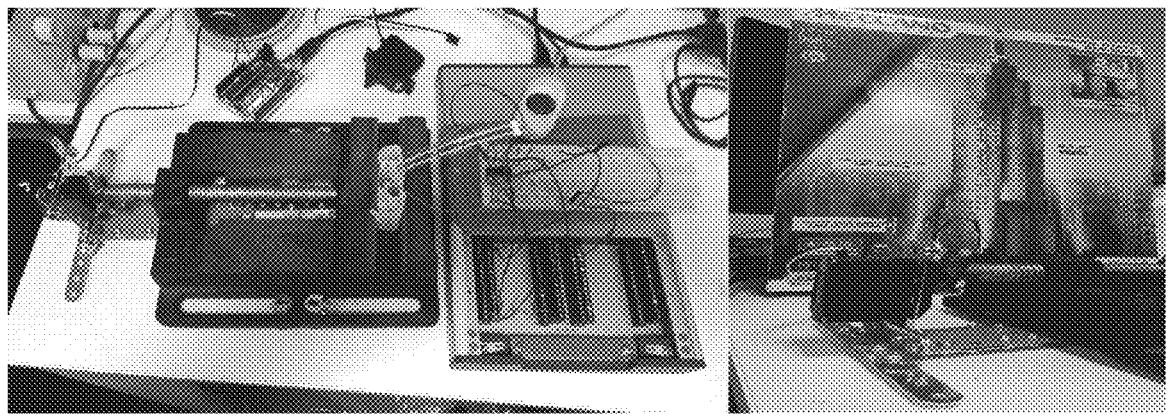
FIG. 3 is an illustration of a sensor characterization setup according to an embodiment of the present disclosure.

Referring to FIG. 3, a linear actuator to characterize a tactile sensor is illustrated. The linear actuator was developed by using a mechanical holding device in which a linear force can by applied by rotation of shaft. A servomotor based system was implemented to control shaft. The assembly of servomotor was developed using a commercial available Meccano structure kit. A conditioning circuit was also used in order to amplify the signal obtained from the tactile sensor along with filtration for smoothing the signal. The signal can be displayed in a graph and also the value of voltage obtained can be digitally displayed for the force reading correspondingly. To characterize the tactile sensor's response to forces applied, a FlexiForce commercial sensor was used to measure defined force reading.

Figure 4:
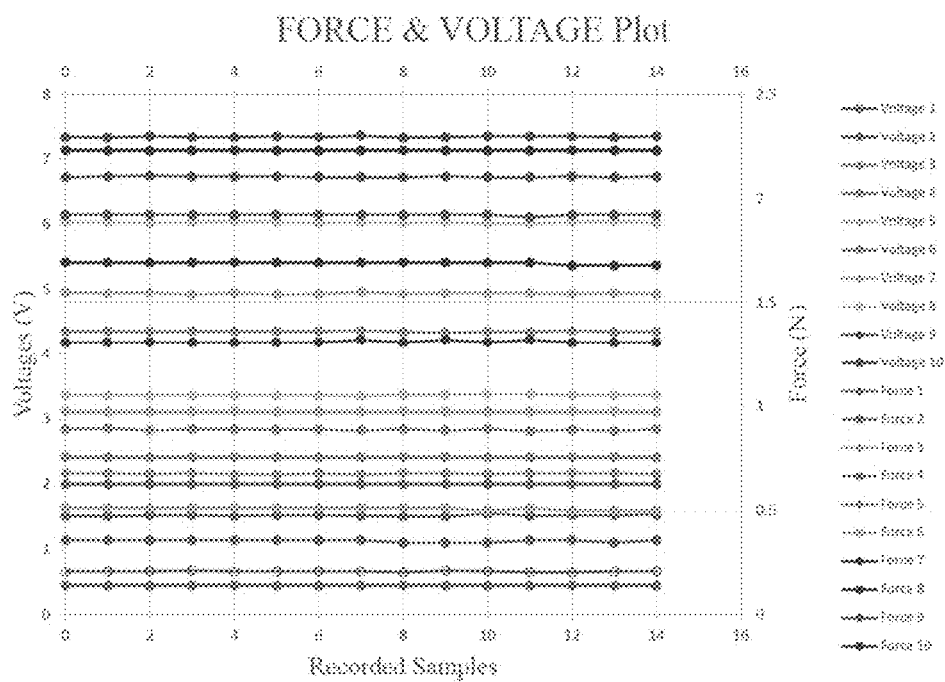
FIG. 4 is a graph of force and voltage readings from a tactile sensor according to an embodiment of the present disclosure.

Referring to FIG. 4, logged data obtained by the forces applied by the linear actuator is illustrated along with the voltage reading from the tactile sensor. The tactile sensor has piezoelectric property. When a force is applied to the tactile sensor, it provides a voltage signal to distinguish the force applied.

Figures 5A, 5B:
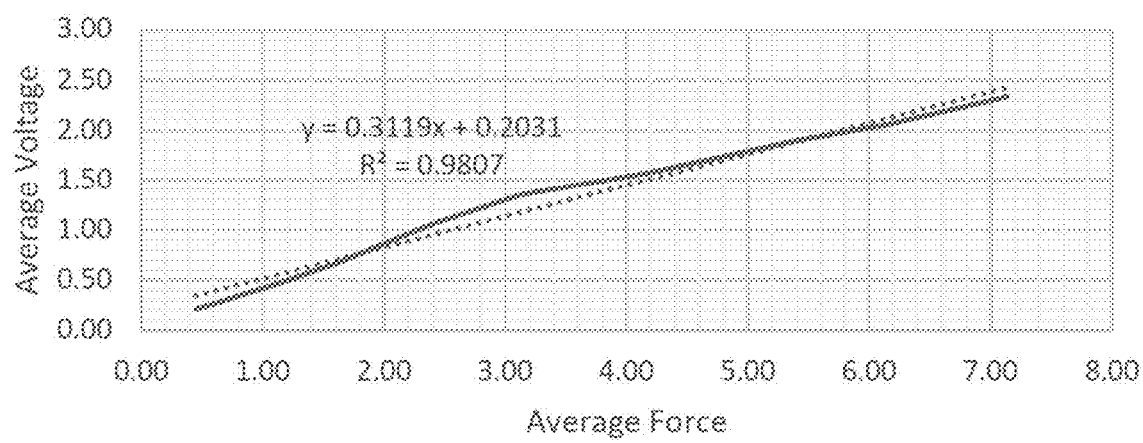
FIGS. 5A and 5B are the data table and a graph of a characteristic curve of a tactile sensor according to an embodiment of the present disclosure.

FIG. 5A illustrates that the tactile sensor will generate an average voltage around 0.21 V when the average force applied to the tactile sensor by the linear actuator is 0.45 Newton (N), and the tactile sensor will generate an average voltage around 2.34 V when the average force applied to the tactile sensor by the linear actuator is 7.14 N. FIG. 5B illustrates a tactile sensor's characteristic curve. The response of the tactile sensor is very stable. The relationship of voltage signal from the tactile sensor follows the linear trend with applied force on the tactile sensor. The tactile sensor is configured to sense a minimum force of as low as 0.5 N.

According to an embodiment of the present disclosure, a tactile sensor may be fabricated using a mixture of polyurethane and zinc oxide. As a non-limiting example, the fabrication of the tactile sensor was conducted as follows:
(1) Prepare a polyurethane (a) and a polyurethane (b);
(2) Mix polyurethane (a) with a solvent (i.e., chloroform);
(3) Mix zinc oxide (5%) with chloroform and stir it overnight;
(4) Sonicate the mixtures of both zinc oxide and polyurethane (a) for 1 hour;
(5) Evaporate the solvent (chloroform) by heating the mixture at 50° C.;
(6) Take the evaporated mixture and mix it with the polyurethane (b) (curing agent);
(7) Turning the mixture into a film in a petri dish;
(8) Cure it at 60° C. for 2 hours;
(9) After obtaining the film, apply silver paste electrodes and highly conductive wire on the film.

According to an embodiment of the present disclosure, a Microporous Polyurethane Thin Layers (MPTL) sensing film is prepared via MPTL fabrication method. The MPTL sensing film is microporous. As a non-limiting example, MPTL sensing film was synthesized using combined techniques of Solvent Casting Particulate Leaching (SC/PL) and Phase Separation (PS). 1,4-dioxane was used as solvent to dissolve the polyurethane composite resin at a concentration of 20% wt/v. In the next step, salt (culineo) having crystals size in the range 0.6-0.4 m was added to the PUR solution until complete saturation was attained. This PUR-salt saturated solution was transplanted in between flat stainless steel molds. The molds were pressed gently in order to obtain uniform distribution throughout the surface. The molds were kept at 30° C. overnight to initiate the process of solvent crystallization. Afterwards, the MPTL was shifted from the mold and kept in warm (60° C.) bi-distilled water. It was fully immersed in water for 5 days with water being changed 2 times per day. This was done in order to wash out the solvent and the sodium particles. In the final step, the sample was dried at 37° C. for 24 h.

According to an embodiment of the present disclosure, the tactile sensor is disposable due to low cost and repeatability in construction.

According to an embodiment of the present disclosure, the tactile sensor has a size of 0.5 cm×0.2 cm area with the thickness of 100 μm. This sophisticated size of the tactile sensor can help to have better integration on the surgical tooltips to provide realistic haptic force feedback for accurate tissue palpation and the identification of contact interactions of the surgical instruments with their patient's tissues and organs.

According to an embodiment of the present disclosure, the tactile sensor is configured to be mounted on a laparoscopic and robotic surgical tooltip using a specialized assembly. The tactile is configured to be strapped over the tip with a non-conductive tape or glued into a cap model which can be easily replaced or disposed of.

According to an embodiment of the present disclosure, the tactile sensor is a single-point force sensor.

According to an embodiment of the present disclosure, the tactile sensor is an array-type sensor that will help in detection and palpation of tissues.

According to an embodiment of the present disclosure, the tactile sensor has a wireless communication unit. The tactile sensor is configured to wirelessly communicate with other devices to transmit data or information obtained during the surgeries, and thus reduces the wire cramping during the surgical tooltip rotation.

According to an embodiment of the present disclosure, the results obtained from the tactile sensor is configured to be presented in a user friendly and interactive Graphical User Interface (GUI) to aid surgeons in surgeries.

According to an embodiment of the present disclosure, the results obtained from the tactile sensor are configured to be developed to a haptic feedback glove to aid the surgeons' hands with the detection of forces applied during surgeries.

According to an embodiment of the present disclosure, the results obtained from the tactile sensor are configured to be used in a clinical study with several surgeons and their valuable feedback will be incorporated into the GUI and a glove with haptic feedback.

According to an embodiment of the present disclosure, the GUI used to present the results of the tactile sensor has force-to-graphical heat maps.

According to an embodiment of the present disclosure, the GUI used to present the results of the tactile sensor has color codes to distinguish forces applied over specific type of surgical instrument used.

According to an embodiment of the present disclosure, the GUI used to present the results of the tactile sensor has inbuilt surgical instruments with 3D structures.

Various non-exhaustive, non-limiting aspects of the present disclosure may be useful alone or in combination with one or more other aspect described herein. Without limiting the foregoing description, in an embodiment of the present disclosure, a tactile sensor is configured to be embedded into surgical instruments. The surface of the tactile sensor is coated and hardened in order to make it durable and resistant to wear and tear even under harsh usage conditions such as during surgeries. The range of the sensible force is wide. The tactile sensor is cost effective and can be easily replaceable or removable from the surgical instruments.

It should be understood that various changes and modifications to the presently preferred embodiments described herein will be apparent to those skilled in the art. Such changes and modifications can be made without departing from the spirit and scope of the present subject matter and without diminishing its intended advantages.

The invention is claimed as follows:

1. A method of producing a tactile sensor, comprising:
    providing a first mixture including polyurethane and a first solvent;
    providing a second mixture including zinc oxide and a second solvent;
    mixing the first mixture with the second mixture to form a third mixture;
    removing solvent from the third mixture;
    adding polyurethane into the third mixture to form a film, and
    providing electrodes on the film.

2. The method of claim 1, wherein at least one of the electrodes includes a silver conductive paste.

3. The method of claim 1, further comprising a first conductive wire and a second conductive wire, wherein the first conductive wire is provided on at least one of the electrodes and the second conductive wire is provided on a second at least one of the electrodes.

4. The method of claim 3, wherein the first conductive wire and the second conductive wire include copper.

5. The method of claim 3, wherein the first conductive wire and the second conductive wire include silver.

6. The method of claim 3, further comprising a top layer and a bottom layer, wherein the top layer is provided on the first conductive wire and the bottom layer is provided on the second conductive wire.

7. The method of claim 6, wherein the top layer and the bottom layer include aluminum.

* * * * *